US011458090B2

(12) United States Patent
Josephson et al.

(10) Patent No.: US 11,458,090 B2
(45) Date of Patent: *Oct. 4, 2022

(54) SPF-ENHANCED WATER-RELEASING SUNSCREEN COMPOSITION

(71) Applicant: L'OREAL, Paris (FR)

(72) Inventors: Lilian Josephson, St. Paul, MN (US); Susan Halpern, Clark, NJ (US); Paul Bonvallet, Newtown, PA (US); Zachary Maron, Clark, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/401,725

(22) Filed: May 2, 2019

(65) Prior Publication Data
US 2020/0368139 A1 Nov. 26, 2020

(51) Int. Cl.
| | |
|---|---|
| A61K 8/894 | (2006.01) |
| A61K 8/81 | (2006.01) |
| A61K 8/25 | (2006.01) |
| A61K 8/27 | (2006.01) |
| A61K 8/29 | (2006.01) |
| A61K 8/37 | (2006.01) |
| A61K 8/58 | (2006.01) |
| A61K 8/06 | (2006.01) |
| A61Q 17/04 | (2006.01) |
| A61K 8/34 | (2006.01) |

(52) U.S. Cl.
CPC ............ A61K 8/894 (2013.01); A61K 8/064 (2013.01); A61K 8/25 (2013.01); A61K 8/27 (2013.01); A61K 8/29 (2013.01); A61K 8/347 (2013.01); A61K 8/37 (2013.01); A61K 8/585 (2013.01); A61K 8/8152 (2013.01); A61Q 17/04 (2013.01); A61K 2800/59 (2013.01)

(58) Field of Classification Search
CPC ........ A61K 8/894; A61K 8/8125; A61K 8/25; A61K 8/27; A61K 8/29; A61K 8/585; A61K 8/064; A61K 8/347; A61K 2800/59; A61Q 17/04

See application file for complete search history.

(56) References Cited

U.S. PATENT DOCUMENTS

| | | | |
|---|---|---|---|
| 6,024,942 A * | 2/2000 | Tanner ................. | A61K 8/8147 424/59 |
| 9,028,804 B2 | 5/2015 | L'Oreal | |
| 9,034,833 B1 | 5/2015 | L'Oreal | |
| 9,549,894 B2 | 1/2017 | L'Oreal | |
| 2007/0009453 A1* | 1/2007 | Willemin ............. | A61K 8/8111 424/59 |
| 2009/0246159 A1* | 10/2009 | Bui ...................... | A61K 8/8111 424/64 |
| 2013/0345315 A1 | 12/2013 | L'Oreal | |
| 2013/0345317 A1 | 12/2013 | L'Oreal | |
| 2019/0374458 A1* | 12/2019 | Bonvallet ............. | A61K 8/891 |

FOREIGN PATENT DOCUMENTS

WO  WO 2016/082061  *  6/2016

OTHER PUBLICATIONS

Non-Final Office Action issued to U.S. Appl. No. 16/001,968 dated Aug. 21, 2019.
Final Office Action issued to U.S. Appl. No. 16/001,968 dated Mar. 18, 2020.
Non-Final Office Action issued to U.S. Appl. No. 16/001,968 dated Sep. 16, 2020.

* cited by examiner

Primary Examiner — Shirley V Gembeh
(74) Attorney, Agent, or Firm — McNees Wallace & Nurick LLC

(57) ABSTRACT

A sunscreen composition includes a silicone phase that includes at least one silicone film former, a blend of silicones that includes at least one of each of a low viscosity silicone fluid, a silicone co-emulsifier and a self-emulsifying silicone elastomer. The composition includes a UV filter system that includes one or more UV filters. The silicone film former and blend of silicones are present in quantities sufficient to provide an SPF that is boosted by at least 100% as compared to a composition that lacks silicone film former, and the cosmetic composition has a unique texture that provides low friction and high glide.

20 Claims, No Drawings

SPF-ENHANCED WATER-RELEASING SUNSCREEN COMPOSITION

FIELD

The present disclosure is directed to skin care compositions that provide UV protection.

BACKGROUND

The photoprotection of keratinous substrates, including both skin and hair, is considered by many to be necessary in order to facilitate protection from sun-damage, sunburn, photo-aging, as well as to decrease the chances of skin cancer development caused by exposure to ultraviolet ("UV") radiation.

It is an object of the present disclosure to provide a composition, in particular a sunscreen composition, that provides SPF protection employing a UV filter system and that is formulated for aesthetically pleasing application to the skin with relatively low friction and high glide. Yet another object of the present disclosure is to provide a favorable environment for skin hydration or skin healing/repair and compatibility with makeup.

SUMMARY

The instant disclosure relates to a sunscreen composition that includes a silicone phase that includes at least one silicone film former present from about 0.1% to about 5.0% by weight, a blend of silicones present from about 20% to about 35% by weight, all based on the total weight of the composition. The blend of silicones includes at least one of each of a low viscosity silicone fluid, a silicone co-emulsifier and a self-emulsifying silicone elastomer. The composition includes a UV filter system that includes one or more UV filters, the UV filter system is present from about 20% to about 30% by weight, based on the total weight of the composition. The silicone film former and blend of silicones are present in quantities sufficient to provide an SPF that is boosted by at least 100% as compared to a composition that lacks silicone film former. In certain embodiments, the composition includes at least two film formers, in some embodiments selected from silicone acrylates film formers. In some embodiments the UV filter system includes one or more mineral based inorganic UV filters or one or more organic UV filters. The composition provides a pleasing tactile feel that is low friction and high glide.

In accordance with some embodiments, the sunscreen composition includes a silicone film former that comprises one or a combination of dimethicone (and) dimethiconol present from about 0.5% to about 2.0% by weight based on the total weight of the composition, and dimethicone (and) acrylates/dimethicone copolymer present from about 2.0% to about 2.5% by weight based on the total weight of the composition. In some embodiments, the sunscreen composition includes at least two or more silicone film formers.

In accordance with some embodiments, the sunscreen composition includes at least one low viscosity silicone fluid in the blend of silicones that comprises one or more volatile and nonvolatile silicone oils. In some embodiments the at least one silicone fluid in the blend of silicones comprises dimethicone present from about 5% to about 18% by weight based on the total weight of the composition.

In accordance with some embodiments, the sunscreen composition includes at least one silicone co-emulsifier that is selected from polyether-modified silicones. In some embodiments, the at least one silicone co-emulsifier in the blend of silicones comprises lauryl PEG-9 polydimethylsiloxyethyl dimethicone present from about 0.2% to about 0.7% by weight based on the total weight of the composition.

In accordance with some embodiments, the sunscreen composition includes at least one self-emulsifying silicone elastomer in the blend of silicones that comprises a substituted or unsubstituted dimethicone crosspolymer. In some embodiments, the at least one self-emulsifying silicone elastomer in the blend of silicones comprises one or more of dimethicone (and) dimethicone/vinyl dimethicone crosspolymer present from about 2% to about 15% by weight based on the total weight of the composition, dimethicone (and) dimethicone/polyglycerin-3 crosspolymer present from about 4% to about 10% by weight based on the total weight of the composition, dimethicone (and) dimethicone/PEG-10/15 crosspolymer present from about 3% to about 7% by weight based on the total weight of the composition, and dimethicone (and) dimethicone crosspolymer present from about 4% to about 8% by weight based on the total weight of the composition.

In accordance with some embodiments, the sunscreen composition is a water-in-silicone emulsion that comprises an aqueous phase, the aqueous phase comprising: a hydrating agent present from about 5% to about 25% by weight, based on the total weight of the composition; and water from about 25% to about 60% by weight based on the total weight of the composition.

In some embodiments, the hydrating agent is glycerin present from about 10% to about 18% by weight based on the total weight of the composition.

In some embodiments, the composition includes one or more of a cosmetic powder, a surfactant, an emollient, and one or more additional additives.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

In the present application, the term "keratinous substrate," as used herein, includes but is not limited to skin, hair, and nails.

As used herein, the term "water-in-silicone" includes a water phase dispersed in an oil phase, where the oil phase is a continuous phase and includes at least one silicone emulsifier.

As used herein, the term "silicone-containing compounds" includes compounds that contain repeating units of siloxane.

"Sun Protection Factor" or SPF is a value expressed mathematically by the ratio of the irradiation time necessary to attain the erythemogenic threshold with the UV screening agent to the time necessary to attain the erythemogenic threshold without the UV screening agent. SPF generally provides information about the skin's resistance to ultraviolet B (UVB) radiation from the sun. The SPF rating system has been developed to provide consumer guidance in selecting sunscreens. All SPF and UV-A ratings are provided on the basis of in-vivo value unless otherwise indicated.

"Critical wavelength" is an absorption spectrum of a sunscreen composition characterized by an index, namely a wavelength, where the integral of the spectral absorbance curve reached 90% of the integral from 290 nm to 400 nm. The critical wavelength is used to determine the breadth of UV protection.

In the present application, the term "stable" means the emulsion remains intact without phase separation, color and/or odor change over the stability monitoring period and the water-soluble active ingredients remain solubilized in the water phase without crystallization or precipitation out of the emulsion. In the present application, the term "ambient temperature" means a temperature of about 25° C.

The instant disclosure provides in various embodiments a sunscreen composition that includes a silicone phase that includes at least one silicone film former present from about 0.1% to about 5.0% by weight, a blend of silicones present from about 20% to about 35% by weight, all based on the total weight of the composition. The blend of silicones includes at least one of each of a low viscosity silicone fluid, a silicone co-emulsifier and a self-emulsifying silicone elastomer. The composition includes a UV filter system that includes one or more UV filters, the UV filter system is present from about 20% to about 30% by weight, based on the total weight of the composition. The silicone film former and blend of silicones are present in quantities sufficient to provide an SPF that is boosted by at least 100% as compared to a composition that lacks silicone film former, and the cosmetic composition has a unique texture that provides low friction and high glide. In accordance with the disclosure, the sunscreen composition includes an aqueous phase that includes water present in the range from about 25% to about 60%. In some embodiments, the aqueous phase also includes one or more hydrating agents present from about 5% to about 25% by weight, all based on the total weight of the composition.

The compositions of the instant disclosure provide an unexpected and unique multifold enhancement of SPF protection in a composition that is aesthetically pleasing, with a light water-releasing property when rubbed on to the skin.

Silicone Phase

In accordance with the disclosure, the silicone phase is present in the composition and includes silicones present in the range from about 20% to about 50% by weight, based on the total weight of the composition. The silicone phase includes at least one silicone film former present in the range from about 0.1% to about 5%, a silicone blend present in the range from about 20% to about 35%, the silicone blend including at least one silicone fluid present in in the range from about 5% to about 20%, at least one silicone co-emulsifier present in the range from about 0.1% to about 2%, and at least one self-emulsifying silicone elastomer present in the range from about 2% to about 15%, all based on the total weight of the composition.

Silicone Film Former

The silicone phase present in the composition according to the disclosure includes at least one silicone film former. A silicone film former may be selected from a silicone acrylate. In some particular embodiments the at least one silicone film former comprises a silicone acrylate co-polymer. Some representative examples of silicone acrylates film formers include dimethicone (and) dimethiconol, dimethicone (and) acrylates/dimethicone copolymer, and acrylates/polytrimethylsiloxymethacrylate copolymer.

In some representative embodiments, a silicone film former is selected from one or a combination of dimethicone (and) dimethiconol, and dimethicone (and) acrylates/dimethicone copolymer.

In accordance with the various embodiments, the amount of silicone film former present in the compositions can range from about 0.1% to about 5.0%, or from about 0.3% to about 3.0%, or from about 0.4% to about 4%, or from about 0.5% to about 2.5%, or any suitable combination, sub-combination, range, or sub-range thereof by weight, based on the weight of the composition. One of ordinary skill in the art, however, will appreciate that other ranges are within the scope of the invention.

Thus, the one or combination of silicone film formers in the composition may be present by weight, based on the total weight of the composition, from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Silicone Blend

In accordance with the various embodiments, the silicone blend is present in the compositions from about 20% to about 35%, or from about 22% to about 33%, or from about 25% to about 30%, or any suitable combination, sub-combination, range, or sub-range thereof by weight, based on the weight of the composition. One of ordinary skill in the art, however, will appreciate that other ranges are within the scope of the invention.

Silicone Fluid

The silicone phase present in the composition according to the disclosure includes at least one low viscosity silicone fluid. In some embodiments, suitable example of silicone fluids include, but are not limited to, volatile or non-volatile polymethylsiloxanes (PDMS) with a linear or cyclic silicone chain, for example, polydimethylsiloxane (dimethicone), and volatile silicone oils, for example cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes, and mixtures thereof.

In some embodiments, suitable example of silicone fluids include, but are not limited to, volatile oils. Volatile oils are cosmetic oils selected from oils having no flash point, oils having a flash point ranging from 40° C. to 100° C., and mixtures thereof, for the purpose of making it easier to employ them. Moreover, they advantageously have a boiling temperature at atmospheric pressure of less than 220° C. and more for example, less than 210° C., in particular ranging from 110 to 210° C. For example, these volatile oils are not monoalcohols containing at least 7 carbon atoms. In some embodiments, volatile oils which can be used according to the disclosure mention may be made of linear or cyclic silicone oils having a viscosity at ambient temperature of less than 8 cSt and having in particular from 2 to 7 silicon atoms, these silicones optionally containing alkyl or alkoxy groups having from 1 to 10 carbon atoms. As volatile silicone oil which can be used in the invention mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyl-tetrasiloxane, dodecamethylpentasiloxane and mixtures thereof.

In accordance with the various embodiments, the amount of low viscosity silicone fluid present in the compositions can range from about 5% to about 20%, or from about 7% to about 18%, or from about 10% to about 15% or any suitable combination, sub-combination, range, or sub-range thereof by weight, based on the weight of the composition. One of ordinary skill in the art, however, will appreciate that other ranges are within the scope of the invention.

Thus, any one of or a combination of low viscosity silicone fluid may be present, by weight, based on the total weight of the composition, is from about 5, 6, 7, 8, 9, 10, 11, 12, 13, 14, 15, 16, 17, 18, 19, to about 20 weight percent, including increments and ranges therein and there between.

Silicone Co-Emulsifier

The silicone phase present in the composition according to the disclosure includes at least one silicone co-emulsifier. Suitable examples of silicone co-emulsifiers include polyether substituted linear or branched polysiloxane copolymers. For example, a silicone co-emulsifier can be selected from dimethicone crosspolymer, dimethicone/vinyl dimethicone crosspolymer, PEG-10 dimethicone, PEG-9 polydimethylsiloxyethyl dimethicone and PEG-9, lauryl PEG-9 polydimethylsiloxyethyl dimethicone, dimethicone, dimethicone(and)dimethicone/PEG-10/15 crosspolymer PEG/PPG-18/18 dimethicone, dimethicone/dimethicone crosspolymer, dimethicone(and)dimethicone/polyglycerin-3 crosspolymer and combinations thereof. One preferred co-emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.). Other suitable co-emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio).

In accordance with the various embodiments, the amount of silicone co-emulsifier present in the compositions can range from about 0.1% to about 2.0%, or from about 0.2% to about 1.8%, or from about 0.5% to about 1.5%, or from about 0.7% to about 1.2%, or any suitable combination, sub-combination, range, or sub-range thereof by weight, based on the weight of the composition. One of ordinary skill in the art, however, will appreciate that other ranges are within the scope of the invention.

Thus, the one or combination of silicone co-emulsifier in the composition may be present by weight, based on the total weight of the composition, from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2 to about 2.0 percent, including increments and ranges therein and there between.

Self-Emulsifying Silicone Elastomer

The silicone phase present in the composition according to the disclosure includes at least one self-emulsifying silicone elastomer. Examples of suitable self-emulsifying silicone elastomers include, but are not limited to, substituted or unsubstituted dimethicone/copolyol crosspolymer, dimethicone(and)dimethicone/vinyldimethicone crosspolymer, dimethicone and dimethicone/PEG-10/15 crosspolymers, substituted or unsubstituted dimethicone/polyglyceral crosspolymer, dimethicone and dimethicone/polyglycerin-3 crosspolymer. Such suitable emulsifying crosslinked siloxane elastomers are sold or made, for example, under the names of "KSG-210" a polyether-modified cross polymer with an INCI name of dimethicone (and) dimethicone/PEG-10/15 crosspolymer, and "KSG-710" a polyglycerin-modified crosspolymer with and INCI name of dimethicone (and) dimethicone/polyglycerin-3 crosspolymer, both available from ShinEtsu Silicones of America, Inc. (Akron, Ohio), PEG-15/lauryl polydimethylsiloxyethyl dimethicone crosspolymer which is sold as a swollen composition comprising silicone oils or other oils, and commercially available under the tradenames KSG-320Z; KSG-350Z; KSG-380Z from Shin-Etsu Chemical Co. The methods of preparing such emulsifying silicone elastomers are disclosed by Sakuta and Tachibana in U.S. Pat. No. 8,592,547, which is hereby incorporated by reference.

In accordance with the various embodiments, the amount of self-emulsifying silicone elastomer present in the compositions can range from about 2% to about 15%, or from about 5% to about 12%, or from about 7% to about 10% or any suitable combination, sub-combination, range, or sub-range thereof by weight, based on the weight of the composition. One of ordinary skill in the art, however, will appreciate that other ranges are within the scope of the invention.

Thus, any one of or a combination of self-emulsifying silicone elastomer may be present, by weight, based on the total weight of the composition, is from about 2, 3, 4, 5, 6, 7, 8, 9, 10, 11, 12, 13, 14, to about 15 weight percent, including increments and ranges therein and there between.

UV Filter System

In accordance with the disclosure, a UV filter system is present in the composition in the range from about 20% to about 30% based on the total weight of the composition.

Examples of suitable UV filters include, but are not limited to, UV filters that are active in UV-A and/or UV-B regions, that may be water-soluble, fat-soluble or insoluble in commonly used cosmetic solvents, and may be inorganic or organic. UV-A filters comprise groups of compounds which absorb light predominantly in the range of wavelengths 400 nm to 320 nm (UV-A) and UV-B filters comprise groups of compounds which absorb light predominantly in the range of wavelengths 400 nm to 320 nm 320 nm to 280 nm (UV-B). According to an embodiment of the disclosure, UV-A and UV-B can be two separate UV filters or they can be one UV filter with both UV-A and UV-B sun protection factor.

Inorganic UV Filters

The composition, according to the present disclosure, may comprise at least one inorganic UV filter. If two or more inorganic UV filters are used, they may be the same or different.

The inorganic UV filter used for the present disclosure may be active in the UV-A and/or UV-B region. The inorganic UV filter may be hydrophilic and/or lipophilic.

The inorganic UV filter is, in some embodiments, insoluble in solvents, such as water, and ethanol commonly used in cosmetics.

It is in some embodiments desirable that the inorganic UV filter be in the form of a fine particle such that the mean (primary) particle diameter thereof ranges from 1 nm to 50 nm, and in some embodiments 5 nm to 40 nm, and in some embodiments 10 nm to 30 nm. The mean (primary) particle size or mean (primary) particle diameter herein is an arithmetic mean diameter.

The inorganic UV filter can be selected from the group consisting of silicon carbide, metal oxides, which may or may not be coated, and mixtures thereof. And in some embodiments, the inorganic UV filters are selected from pigments (mean size of the primary particles: generally from 5 nm to 50 nm, and in some embodiments from 10 nm to 50 nm) formed of metal oxides, such as, for example, pigments formed of titanium oxide (amorphous or crystalline in the rutile and/or anatase form), iron oxide, zinc oxide, zirconium oxide, or cerium oxide, which are all UV photoprotective agents that are well known per se. And in some embodiments, the inorganic UV filters are selected from titanium oxide, and zinc oxide, and in some particular embodiments, titanium oxide.

The inorganic UV filter may or may not be coated. The inorganic UV filter may have at least one coating. The coating may comprise at least one compound selected from the group consisting of alumina, silica, aluminum hydroxide, silicones, silanes, fatty acids or salts thereof (such as sodium, potassium, zinc, iron, or aluminum salts), fatty alcohols, lecithin, amino acids, polysaccharides, proteins, alkanolamines, waxes, such as beeswax, (meth)acrylic polymers, organic UV filters, and (per)fluoro compounds. It is in some embodiments desirable for the coating to include at least one organic UV filter. As the organic UV filter in the coating, a dibenzoylmethane derivative, such as butyl methoxydibenzoylmethane (Avobenzone) and 2,2'-Methylenebis[6-(2H-Benzotriazol-2-yl)-4-(1,1,3,3-Tetramethyl-Butyl) Phenol] (Methylene Bis-Benzotriazolyl Tetramethylbutylphenol) marketed as "TINOSORB M" by BASF, may be desirable.

Of course, the inorganic UV filter made of metal oxides may, before their treatment with silicones, have been treated with other surfacing agents, in particular, with cerium oxide, alumina, silica, aluminum compounds, silicon compounds, or their mixtures. The coated inorganic UV filter may have been prepared by subjecting the inorganic UV filter to one or more surface treatments of a chemical, electronic, mechano-chemical, and/or mechanical nature with any of the compounds as described above, as well as polyethylenes, metal alkoxides (titanium or aluminum alkoxides), metal oxides, sodium hexametaphosphate, and those shown, for example, in Cosmetics & Toiletries, February 1990, Vol. 105, pp. 53-64.

The coated inorganic UV filter may be titanium oxides coated: with silica, such as the product "Sun veil" from Ikeda, and "Sunsil TIN 50" from Sunjin Chemical; with silica and with iron oxide, such as the product "Sunveil F" from Ikeda; with silica and with alumina, such as the products "Microtitanium Dioxide MT 500 SA" from Tayca, "Tioveil" from Tioxide, and "Mirasun TiW 60" from Rhodia; with alumina, such as the products "Tipaque TTO-55 (B)" and "Tipaque TTO-55 (A)" from Ishihara, and "UVT 14/4" from Kemira; with alumina and with aluminum stearate, such as the product "Microtitanium Dioxide MT 100 T, MT 100 TX, MT 100 Z or MT-01" from Tayca, the products "Solaveil CT-10 W" and "Solaveil CT 100" from Uniqema, and the product "Eusolex T-AVO" from Merck; with alumina and with aluminum laurate, such as the product "Microtitanium Dioxide MT 100 S" from Tayca; with iron oxide and with iron stearate, such as the product "Microtitanium Dioxide MT 100 F" from Tayca; with zinc oxide and with zinc stearate, such as the product "BR351" from Tayca; with silica and with alumina and treated with a silicone, such as the products "Microtitanium Dioxide MT 600 SAS", "Microtitanium Dioxide MT 500 SAS", and "Microtitanium Dioxide MT 100 SAS" from Tayca; with silica, with alumina and with aluminum stearate and treated with a silicone, such as the product "STT-30-DS" from Titan Kogyo; with silica and treated with a silicone, such as the product "UV-Titan X 195" from Kemira; with alumina and treated with a silicone, such as the products "Tipaque TTO-55 (S)" from Ishihara or "UV Titan M 262" from Kemira; with triethanolamine, such as the product "STT-65-S" from Titan Kogyo; with stearic acid, such as the product "Tipaque TTO-55 (C)" from Ishihara; or with sodium hexametaphosphate, such as the product "Microtitanium Dioxide MT 150 W" from Tayca. Other titanium oxide pigments treated with a silicone are, and in some embodiments TiO2 treated with octyltrimethylsilane and for which the mean size of the individual particles is from 25 and 40 nm, such as that marketed under the trademark "T 805" by Degussa Silices, TiO2 treated with a polydimethylsiloxane and for which the mean size of the individual particles is 21 nm, such as that marketed under the trademark "70250 Cardre UF TiO2Si3" by Cardre, and anatase/rutile TiO2 treated with a polydimethylhydrosiloxane and for which the mean size of the individual particles is 25 nm, such as that marketed under the trademark "Microtitanium Dioxide USP Grade Hydrophobic" by Color Techniques.

And in some embodiments, the following coated TiO2 can be used as the coated inorganic UV filter: Stearic acid (and) Aluminum Hydroxide (and) TiO2, such as the product "MT-100 TV" from Tayca, with a mean primary particle diameter of 15 nm; Dimethicone (and) Stearic Acid (and) Aluminum Hydroxide (and) TiO2, such as the product "S A-TTO-S4" from Miyoshi Kasei, with a mean primary particle diameter of 15 nm; Silica (and) TiO2, such as the product "MT-100 WP" from Tayca, with a mean primary particle diameter of 15 nm; Dimethicone (and) Silica (and) Aluminum Hydroxide (and) TiO2, such as the product "MT-Y02" and "MT-Y-110 M3S" from Tayca, with a mean primary particle diameter of 10 nm; Dimethicone (and) Aluminum Hydroxide (and) TiO2, such as the product "SA-TTO-S3" from Miyoshi Kasei, with a mean primary particle diameter of 15 nm; Dimethicone (and) Alumina (and) TiO2, such as the product "UV TITAN M1 70" from Sachtleben, with a mean primary particle diameter of 15 nm; and Silica (and) Aluminum Hydroxide (and) Alginic Acid (and) TiO2, such as the product "MT-100 AQ" from Tayca, with a mean primary particle diameter of 15 nm. In terms of UV filtering ability, TiO2 coated with at least one organic UV filter is more desirable. For example, Avobenzone (and) Stearic Acid (and) Aluminum Hydroxide (and) TiO2, such as the product "HXMT-100ZA" from Tayca, with a mean primary particle diameter of 15 nm, can be used.

The uncoated titanium oxide pigments are, for example, marketed by Tayca under the trademarks "Microtitanium Dioxide MT500B" or "Microtitanium Dioxide MT600B", by Degussa under the trademark "P 25", by Wacker under the trademark "Oxyde de titane transparent PW", by Miyoshi Kasei under the trademark "UFTR", by Tomen under the trademark "ITS" and by Tioxide under the trademark "Tioveil AQ". The uncoated zinc oxide pigments are, for example: those marketed under the trademark "Z-cote" by Sunsmart; those marketed under the trademark "Nanox" by Elementis; and those marketed under the trademark "Nanogard WCD 2025" by Nanophase Technologies. The coated zinc oxide pigments are, for example: those marketed under the trademark "Oxide Zinc CS-5" by Toshiba (ZnO coated with polymethylhydrosiloxane); those marketed under the trademark "Nanogard Zinc Oxide FN" by Nanophase Technologies (as a 40% dispersion in Finsolv TN, C12-C15 alkyl benzoate); those marketed under the trademark "Daitopersion Zn-30" and "Daitopersion Zn-50" by Daito (dispersions in oxyethylenated polydimethylsiloxane/cyclopolymethylsiloxane comprising 30% or 50% of zinc nano-oxides coated with silica and polymethylhydrosiloxane); those marketed under the trademark "NFD Ultrafine ZnO" by Daikin (ZnO coated with phosphate of perfluoroalkyl and a copolymer based on perfluoroalkylethyl as a dispersion in cyclopentasiloxane); those marketed under the trademark "SPD-Z1" by Shin-Etsu (ZnO coated with a silicone-grafted acrylic polymer dispersed in cyclodimethylsiloxane); those marketed under the trademark "Escalol Z100" by ISP (alumina-treated ZnO dispersed in an ethylhexyl methoxycinnamate/PVP-hexadecene copolymer/methicone mixture); those marketed under the trademark "Fuji ZnO-SMS-10" by Fuji Pigment (ZnO coated with silica and polymethylsilsesquioxane); and those marketed under the trademark "Nanox Gel TN" by Elementis (ZnO dispersed at 55% in C12-C15 alkyl benzoate with hydroxystearic acid polycondensate). The uncoated cerium oxide pigments are marketed, for example, under the trademark "Colloidal Cerium Oxide" by Rhone-Poulenc.

The uncoated iron oxide pigments are, for example, marketed by Arnaud under the trademarks "Nanogard WCD 2002 (FE 45B)", "Nanogard Iron FE 45 BL AQ", "Nanogard FE 45R AQ", and "Nanogard WCD 2006 (FE 45R)", or by Mitsubishi under the trademark "TY-220". The coated iron oxide pigments are, for example, marketed by Arnaud under the trademarks "Nanogard WCD 2008 (FE 45B FN)", "Nanogard WCD 2009 (FE 45B 556)", "Nanogard FE 45 BL 345", and "Nanogard FE 45 BL", or by BASF under the trademark "Oxyde de fer transparent".

Mention may also be made of mixtures of metal oxides, in particular, of titanium dioxide and of cerium dioxide, including a mixture of equal weights of titanium dioxide coated with silica and of cerium dioxide coated with silica marketed by Ikeda under the trademark "Sunveil A", and also a mixture of titanium dioxide and of zinc dioxide coated with alumina, with silica and with silicone, such as the product "M 261" marketed by Kemira, or coated with alumina, with silica and with glycerol, such as the product "M 211" marketed by Kemira. Coated inorganic UV filters are desirable, because the UV filtering effects of the inorganic UV filters can be enhanced. In addition, the coating(s) may help uniformly or homogeneously disperse the UV filters in the composition, according to the present disclosure.

Organic UV Filter

The compositions, according to the disclosure, may comprise at least one organic UV filter. If two or more organic UV filters are used, they may be the same or different.

The organic UV filter used for the present disclosure may be active in the UV-A and/or UV-B region. The organic UV filter may be hydrophilic and/or lipophilic. The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from a-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof. Anthranilic compounds: Menthyl anthranilate, marketed under the trademark "Neo Heliopan MA" by Haarmann and Reimer. Dibenzoylmethane compounds: Butyl methoxydibenzoylmethane, marketed, in particular, under the trademark "Parsol 1789" by Hoffmann-La Roche; and isopropyl dibenzoylmethane. Cinnamic compounds: Ethylhexyl methoxycinnamate, marketed, in particular, under the trademark "Parsol MCX" by Hoffmann-La Roche; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methyl cinnamate; and glyceryl ethylhexanoate dimethoxycinnamate. Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer. Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex. Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethylamino-2-hydroxybenzoyl)benzoate (UVINUL A+ by BASF). β,β-Diphenyl acrylate compounds: Octocrylene, marketed in particular under the trademark "Uvinul N539" by BASF; and Etocrylene, marketed in particular under the trademark "Uvinul N35" by BASF. Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVTNUL T150» by BASF. Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975. Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche. Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer. Imidazoline compounds: Ethylhexyl dimethoxybenzylidene dioxoimidazoline propionate. Bis-benzoazolyl compounds: The derivatives as described in EP-669,323 and U.S. Pat. No. 2,463,264. Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed, in particular, under the trademark "Escalol 507" by ISP, glyceryl PABA, and PEG-25 PABA, marketed under the trademark "Uvinul P25" by BASF. Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or "Mexoryl XL" by L'Oreal. Benzoxazole compounds: 2,4-bis[5-1(dimethylpropyl)benzoxazol-2-yl-(4-phenyl)imino]-6-(2-ethylhexyl)imino-1,3,5-triazine, marketed under the trademark of Uvasorb K2A by Sigma 3V. Screening polymers and screening silicones: The silicones described in WO 93/04665. Dimers derived from a-alkylstyrene: The dimers described in DE-19855649. 4,4-Diarylbutadiene compounds: 1,1-dicarboxy(2,2'-dimethylpropyl)-4,4-diphenylbutadiene.

In some embodiments the organic UV filter(s) may be selected from the group consisting of: butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 1,r-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-amino-benzalmalonate)-6-[(3-{1,3,3,3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutylphenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1(dimethylpropyl) benzoxazol-2-yl-(4-phenyl)imino]-6-(2-ethylhexyl)imino-1,3,5-triazine, camphor benzylkonium methosulfate, and mixtures thereof.

In accordance with the various embodiments, the amount of each UV filter present in the compositions can range from about 2% to about 15%, or from about 5% to about 12%, or from about 7% to about 10% or any suitable combination, sub-combination, range, or sub-range thereof by weight, based on the weight of the composition. One of ordinary skill in the art, however, will appreciate that other ranges are within the scope of the invention.

Thus, any one of the UV filters may be present, by weight, based on the total weight of the composition, is from about 2, 3, 4, 5, 6, 7, 8, 9, 10, 11, 12, 13, 14, to about 15 weight percent, including increments and ranges therein and there between.

In accordance with the various embodiments, the total amount of UV filters present in the systems and compositions can range from about 20% to about 30%, or from about 22% to about 28%, or from about 24% to about 26%, or any suitable combination, sub-combination, range, or sub-range thereof by weight, based on the weight of the composition. One of ordinary skill in the art, however, will appreciate that other ranges are within the scope of the invention.

Thus, the combination of UV filters present, by weight, based on the total weight of the composition, is from about 20, 21, 22, 23, 24, 25, 26, 27, 28, 29, to about 30 weight percent, including increments and ranges therein and there between.

Emollients

The composition according to the disclosure may include one or more emollients. Examples of emollients that may be included in the compositions include:

Suitable emollients include fatty acid ester emollients derived from C12-C50 fatty acids, for example, C16-C22 saturated fatty acids, and monohydric alcohols. Examples of such esters include isopropyl myristate, methyl palmitate, isopropyl laurate, isopropyl palmitate, ethylhexyl palmitate, myristyl myristate, and mixtures thereof.

Suitable emollients include hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol® 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate; fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew® SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam® oil, or the mixture of n-undecane ($C_{11}$) and of n-tridecane ($C_{13}$) sold under the reference Cetiol® UT by the company Cognis; fluoro oils that are partially hydrocarbon-based and/or silicone-based, for instance those described in document JP-A-2 295 912; mixtures thereof.

Additional examples of suitable emollients include benzoic acid esters of $C_9$-$C_{15}$ alcohols, isononyl iso-nonanoate, $C_{12}$-$C_{15}$ alkyl benzoate, or any combinations thereof.

Additional examples of emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of $C_9$-$C_{15}$ alcohols, isononyl iso-nonanoate, alkanes, mineral oil, silicone, dimethyl polysiloxane, ether, polyoxypropylene butyl ether, polyoxypropylene cetyl ether, $C_{12}$-$C_{15}$ alkyl benzoate, aryl alkyl benzoate, Isopropyl Lauroyl sarcosinate, and any combinations thereof.

Suitable emollients include fatty acid triglyceride emollients, including those which are synthetic or naturally occurring. Fatty acid triglycerides are generally fatty acid triesters of glycerol, the fatty acids of which may have chain lengths from C4 to C24, these chains possibly being linear or branched, and saturated or unsaturated. Examples of such fatty acid triglyceride emollients include wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, safflower oil, and caprylic/capric acid triglycerides.

Suitable monocarboxylic acid ester emollients include those of the general formula R'COOR, wherein R' and R are straight or branched chain, saturated or unsaturated alkyl, aryl, and wherein sum of carbon atoms in R' and R is at least 10. A suitable monoester is alkyl benzoate such as C12-15 alkyl benzoate.

Suitable synthetic ether emollients include those containing from 10 to 40 carbon atoms, such as dicaprylyl ether. Suitable sorbitan fatty acid ester emollients include sorbitan oleates such as sorbitan trioleate.

The compositions according to the disclosure may comprise one or more volatile hydrocarbon-based oils. As volatile hydrocarbon-based oils that may be used according to the disclosure, mention may be made especially of hydrocarbon-based oils containing from 8 to 16 carbon atoms, and especially branched C8-C16 alkanes such as C8-C16 isoalkanes of petroleum origin (also known as isoparaffins), for instance isododecane (also known as 2,2,4,4,6-pentamethylheptane), isodecane, and isohexadecane.

In accordance with the various embodiments, the amount of emollient present in the compositions can range from about 1% to about 10%, or from about 2% to about 8% or from about 4% to about 6% or any suitable combination, sub-combination, range, or sub-range thereof by weight, based on the weight of the composition. One of ordinary skill in the art, however, will appreciate that other ranges are within the scope of the invention.

Thus, any one of or a combination of emollient may be present, by weight, based on the total weight of the composition, is from about 1, 2, 3, 4, 5, 6, 7, 8, 9, to about 10 weight percent, including increments and ranges therein and there between.

Cosmetic Powder

The cosmetic composition of the present disclosure may include at least one cosmetic powder. Representative cosmetic powders may be selected, in some embodiments, from polymer based microspheres, in particular, plastic microspheres, that include, but are not limited to, methyl methacrylate crosspolymer, HDI/trimethyl hexyllactone crosspolymer, Ethylene/Methacrylate Copolymer, polylactic acid, polymethylsilsesquioxane, polymethyl methylacrlyate, methylmethacrylate crosspolymer, ethylene, acrilyic acid copyolymer, aluminimum chlorohudrate, polyethylene, acrylates/ethylhexyl acrylate crosspolymer (and) sodiumpolyacrylate, polylactic acid (and) polyglyceryl-5 laurate, and combinations thereof.

In accordance with the various embodiments, the amount of cosmetic powder that may be present in the compositions can range from about 0.1% to about 5.0%, or from about 0.3% to about 3.0%, or from about 0.4% to about 4%, or from about 0.5% to about 2.5%, or any suitable combination, sub-combination, range, or sub-range thereof by weight, based on the weight of the composition. One of ordinary skill in the art, however, will appreciate that other ranges are within the scope of the invention.

Thus, the one or combination of cosmetic powder in the composition may be present by weight, based on the total weight of the composition, from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Aqueous Phase

In accordance with the disclosure, the aqueous phase is present in the composition and includes water present in the range from about 25% to about 60%. In some embodiments, the aqueous phase also includes one or more hydrating agent present from about 5% to about 25% by weight, all based on the total weight of the composition.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition is not limited but is generally between 2 and 12, and in some embodiments, is one of between 3 and 11, and between 5 and 9, and between 6 and 8, and in some embodiments is 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Hydrating Agent

In accordance with the disclosure, one more hydrating agents may be present in the composition. The hydrating agent present in the cosmetic composition, according to the disclosure, includes, but is not limited to, one or more of polyols, including, for example, glycerin, glycerol, glycols, such as caprylyl glycol, butylene glycol, propylene glycol, isoprene glycol, dipropylene glycol, hexylene glycol and polyethylene glycols, monoethylene glycol, diethylene glycol, triethylene glycol, diethylene glycol, hexylene glycol, glycol ethers such as monopropylene, dipropylene and tripropylene glycol alkyl(C1-C4)ethers, squalane, triacetin, sugars, such as glucose, xylitol, maltitol, sorbitol, sucrose pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract.

Suitable examples of the hydrating agent include polyols, for example, glycerin and caprylyl glycol.

In accordance with the various embodiments, the amount of hydrating agent present in the compositions can range from about 5% to about 25%, or from about 10% to about 20%, or from about 10% to about 15% or any suitable combination, sub-combination, range, or sub-range thereof by weight, based on the weight of the composition. One of ordinary skill in the art, however, will appreciate that other ranges are within the scope of the invention.

Thus, any one of or a combination of hydrating agent may be present, by weight, based on the total weight of the composition, is from about 5, 6, 7, 8, 9, 10, 11, 12, 13, 14, 15, 16, 17, 18, 19, 20, 21, 22, 23, 24, to about 25 weight percent, including increments and ranges therein and there between.

Surfactant

In accordance with the disclosure, one or more surfactants may be present in the composition. The surfactants present in the cosmetic composition, according to the disclosure, includes, but is not limited to, one or more of surfactants selected from hydrocarbon-based surfactants resulting from the esterification of a mixture of polyglycerol with (i) a polyhydroxystearic acid, with 2 to 5 polyglycerol units (for example, 4 units), (ii) linear or branched aliphatic dicarboxylic acids containing 4 to 14 carbon atoms, for example, sebacic acid, and (iii) saturated or unsaturated, linear or branched fatty acids containing from 16 to 20 carbon atoms, for example, isostearic acid.

In accordance with the disclosure, by way of non-limiting example, the one or more surfactant in the emulsion may be chosen from a polyhydroxystearic acid ester of polyglycerol. In one embodiment, the surfactant includes polyglyceryl-4 diisostearate polyhydroxystearate sebacate, commercially available under the name Isolan GPS by the company Evonik Goldschmidt.

In accordance with the various embodiments, the amount of surfactant that may be present in the compositions can range from about 1% to about 10%, or from about 2% to about 8% or from about 4% to about 6% or any suitable combination, sub-combination, range, or sub-range thereof by weight, based on the weight of the composition. One of ordinary skill in the art, however, will appreciate that other ranges are within the scope of the invention.

Thus, any one of or a combination of surfactant may be present, by weight, based on the total weight of the composition, is from about 1, 2, 3, 4, 5, 6, 7, 8, 9, to about 10 weight percent, including increments and ranges therein and there between.

Optional Ingredients

In accordance with the disclosure, in some embodiments, there may be one or more actives present in the cosmetic composition in one or both of the silicone and the aqueous phases. In some embodiments, additives used according to the disclosure may be selected from actives, including but not limited to: anti-microbial components, including, but not limited to, caprylyl glycine and sodium salicylate; antioxidants, including, but not limited to, phenolic compounds, such as chalcones, flavones, flavanones, flavanols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, phenolic terpenes, resveratrol, curcumin, pinoresinol, ferulic acid, hydroxytyrosol, cinnamic acid, caffeic acid, p-coumaric acid, baicalin, pine bark extract, ellagic acid; and vitamins and vitamin derivatives, such as panthenol, tocopherol, ascorbic acid; conditioning agents such as the silicone oil dimethicone, allantoin and dicaprylyl carbonate; clays such as kaolin; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example Pyrus Malus (Apple) Fruit Extract, and Aloe Barbadensis Leaf Juice Powder; citric acid, sodium chloride; acetyl trifluoromethylphenyl valylglycine and combinations thereof. Although the optional active additives are given as examples, it will be appreciated that other optional components compatible with cosmetic applications known in the art may be used.

Also, in accordance with the disclosure, in some embodiments, there may be one or more other cosmetically acceptable additives present in the cosmetic composition. In some embodiments, cosmetically acceptable additives used according to the disclosure may be selected from colorants, preservatives, fragrances, dyes, neutralizing or pH-adjusting agents (e.g., triethylamine (TEA) and sodium hydroxide). Although the optional additives are given as examples, it will be appreciated that other optional components compatible with cosmetic applications known in the art may be used.

In some particular embodiments, the composition includes one or a combination of actives and additives selected from sodium citrate, potassium phosphate, dipotassium phosphate, acetyl trifluoromethylphenyl valylglycine, citric acid, phenoxyethanol, and caprylyl glycol.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.05% to about 0.1%, or from about 0.15% to about 5%, or from about 0.40% to about 4%, or from about 0.5% to about 2% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Preservative System

The composition according to the disclosure may include a preservative system. In some embodiments, the preservative system includes one or more preservatives, the one or combination present at a concentration, by weight of about 0.1% to about 3%, or alternatively about 0.5% to about 2.5% or alternatively about 1% to about 2.0%, based upon weight of the composition. In a preferred embodiment, the preservative system comprises organic acids, parabens, formaldehyde donors, phenol derivatives, quaternary ammoniums, alcohols, isothiazolinones, and combinations thereof.

Examples of organic acid preservative systems include, but are not limited to, sodium benzoate, potassium sorbate, benzoic acid and dehydroacetic acid, sorbic acid, and combinations thereof. A preferred organic acid preservative system includes a mixture of sodium benzoate and potassium sorbate.

Examples of paraben preservative systems include, but are not limited to, alkyl para-hydroxybenzoates, wherein the alkyl radical has from 1, 2, 3, 4, 5 or 6 carbon atoms and for example, from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben).

Examples of formaldehyde donor preservative systems include, but are not limited to, 1,3-Dimethylol-5,5-dimethylhydantoin (DMDM hydantoin), imidazolidinyl urea, gluteraldehyde, and combinations thereof.

Examples of quaternary ammonium preservative systems include, but are not limited to, benzalkonium chloride, methene ammonium chloride, benzethonium chloride, and combinations thereof.

Examples of alcohol preservative systems include, but are not limited to, ethanol, benzyl alcohol, dichlorobenzyl alcohol, phenoxyethanol, and combinations thereof.

Examples of isothiazolone preservative systems include, but are not limited to, methylchloroisothiazolinone, methylisothiazolinone, and combinations thereof.

Other suitable preservatives for preservative systems include, but are not limited to, chloracetamide, triclosan and iodopropynyl butylcarbamate, pyridine derivatives (e.g., pyrithione and zinc pyrithione), chlorphenesin, phenyl mercuric salts, phenoxyethanol, and other known preservative systems.

Fragrance

The composition according to the disclosure may include one or more fragrances. Fragrances including natural or synthetic odoriferous substances or mixtures thereof may be included in the cosmetic composition of the present disclosure. Use may be made of mixtures of different odoriferous substances which together generate an attractive scent. Natural odoriferous substances are extracts of flowers (lily, lavender, rose, jasmine, neroli or ylang-ylang), stems and leaves (geranium, patchouli, petitgrain), fruits (anis, coriander, caraway, juniper), fruit rinds (bergamot, lemon, orange), roots (mace, angelica, celery, cardamom, costus, iris, thyme), needles and twigs (spruce, fir, pine, mountain pine) and resins and balsams (galbanum, elemi, benzoin, myrrh, frankincense, opoponax). Typical synthetic perfume compounds are products of the esters, ethers, aldehydes, ketones, alcohols and hydrocarbon types. Essential oils of low volatility, which are generally used as flavoring components, are also suitable as fragrances, for example, but not limited to, sage oil, camomile oil, clove oil, balm oil, peppermint oil, cinnamon leaf oil, linden blossom oil, juniper berry oil, vetiver oil, frankincense oil, galbanum oil, labdanum oil and lavandin oil.

The following examples are intended to further illustrate the present invention. They are not intended to limit the invention in any way. Unless otherwise indicated, all parts are by weight.

EXAMPLES

The following Examples are provided for illustrative purposes only and are not intended to be limiting.

Raw Materials

Compositions as described herein according to the disclosure, and compositions as exemplified herein include raw materials selected from commercially available materials. In the examples, all raw materials are used at concentrations of 100% unless otherwise noted including, for example:

Example 1: Inventive Examples and Comparative (Control)

The following compositions exemplify certain embodiments according to the disclosure.

TABLE 1

Examples of Inventive and Comparative Compositions

| INGREDIENT | INV 1 SPF | COMP SPF; NO FILM FORMER | INV 2 SPF | INV 3 SPF 30 | INV 4 SPF 30 | INV 5 SPF | INV 6 SPF 50 |
| --- | --- | --- | --- | --- | --- | --- | --- |
| Sodium Citrate | 0.5 | 0.5 | | 0.5 | 0.5 | 0.5 | 0.5 |
| Potassium Phosphate | | | 0.6 | | | | |
| Dipotassium Phosphate | | | 0.4 | | | | |
| Acetyl Trifluoromethylphenyl Valylglycine | | | 1 | | | | |
| Citric Acid | 0.35 | 0.35 | 0.05 | 0.2 | 0.2 | 0.2 | 0.2 |
| Ethylhexyl Palmitate | | | 5 | | | | |
| Phenoxyethanol | 0.6 | 0.6 | 0.6 | 0.6 | 0.6 | 0.6 | 0.6 |

TABLE 1-continued

Examples of Inventive and Comparative Compositions

| INGREDIENT | INV 1 SPF | COMP SPF; NO FILM FORMER | INV 2 SPF | INV 3 SPF 30 | INV 4 SPF 30 | INV 5 SPF | INV 6 SPF 50 |
|---|---|---|---|---|---|---|---|
| Dimethicone | 5 | 5 | | 16.5 | 17.25 | 16.5 | 16.5 |
| Dimethicone (And) Dimethicone/Vinyl Dimethicone Crosspolymer | 13.5 | 13.5 | | | | | |
| Dimethicone (And) Dimethiconol | 0.5 | | 10 | 0.25 | | 0.25 | 0.25 |
| Dimethicone (And) Dimethicone/PEG-10/15 Crosspolymer | | | | 5 | 5 | 5 | 5 |
| Lauryl Peg-9 Polydimethylsiloxyethyl Dimethicone | 0.5 | 0.5 | | 1 | 1 | 1 | 1 |
| Dimethicone (And) Dimethicone/ Polyglycerin-3 Crosspolymer | 8.5 | 8.5 | | | | | |
| Dimethicone (And) Acrylates/Dimethicone Copolymer | 2 | | | 0.5 | | 0.5 | 0.5 |
| Dimethicone (And) Dimethicone Crosspolymer | | | 7 | 7.5 | 7.5 | 7.5 | 7.5 |
| Dimethicone (And) Dimethicone/Vinyl Dimethicone Crosspolymer | | | | 3.5 | 3.5 | 3.5 | 3.5 |
| Water | 10 | 10 | | 20 | 20 | 10 | 20 |
| Glycerin | 15 | 15 | 15 | 15 | 15 | 15 | 15 |
| Caprylyl Glycol | 0.3 | 0.3 | | 0.3 | 0.3 | 0.3 | 0.3 |
| Butyl Methoxydibenzoylmethane | 2.63 | 2.63 | | | | | |
| Ethylhexyl Salicylate | 4.33 | 4.33 | | | | | |
| ZINC OXIDE (And) TRIETHOXYCAPRYLYLSILANE | | | | 5 | 5 | 5 | 15.38 |
| Octocrylene | 5.25 | 5.25 | | | | | |
| Homosalate | 7.79 | 7.79 | | | | | |
| Titanium Dioxide | | | | 5 | 5 | 9 | |
| Titanium Dioxide (And) Silica | | | | | | | 6.35 |
| Polyglyceryl-4 Diisostearate/ Polyhydroxystearate/Sebacate | | | 3 | | | | |
| Panthenol | 5 | 5 | 1 | 5 | 5 | 5 | 5 |
| Water | 18.25 | 20.75 | 56.35 | 14.15 | 14.15 | 10.15 | 2.42 |

TABLE 3

Inventive Examples Continued

| INGREDIENT | INV 7 SPF | INV 8 SPF | INV 9 SPF | INV 10 SPF | INV 11 2X FILM FORMER | INV 12 SPF | INV 13 SPF |
|---|---|---|---|---|---|---|---|
| Sodium Citrate | 0.5 | 0.5 | 0.5 | 0.5 | 0.5 | 0.5 | 0.5 |
| Potassium Phosphate | | | | | | | |
| Dipotassium Phosphate | | | | | | | |
| Acetyl Trifluoromethylphenyl Valylglycine | | | | | | | |
| Citric Acid | 0.2 | 0.2 | 0.2 | 0.2 | 0.2 | 0.2 | 0.2 |
| Ethylhexyl Palmitate | | | | | | | |
| Phenoxyethanol | 0.6 | 0.6 | 0.6 | 0.6 | 0.6 | 0.6 | 0.6 |
| Dimethicone | 29.5 | 26.5 | 31 | 33 | 33 | 33 | 33 |
| Dimethicone (And) Dimethicone/Vinyl Dimethicone Crosspolymer | | | | | | | |
| Dimethicone (And) Dimethiconol | 0.25 | 0.25 | 0.25 | 0.25 | 0.5 | 0.25 | 0.5 |
| Dimethicone (And) Dimethicone/PEG-10/15 Crosspolymer | 5 | 5 | 5 | 5 | 5 | 5 | 5 |

TABLE 3-continued

Inventive Examples Continued

| INGREDIENT | INV 7 SPF | INV 8 SPF | INV 9 SPF | INV 10 SPF | INV 11 2X FILM FORMER | INV 12 SPF | INV 13 SPF |
|---|---|---|---|---|---|---|---|
| Lauryl Peg-9 Polydimethylsiloxyethyl Dimethicone | 1 | 1 | 1 | 1 | 1 | 1 | 1 |
| Dimethicone (And) Dimethicone/ Polyglycerin-3 Crosspolymer | | | | | | | |
| Dimethicone (And) Acrylates/Dimethicone Copolymer | 0.5 | 0.5 | 0.5 | 0.5 | 1 | 0.5 | 1 |
| Dimethicone (And) Dimethicone Crosspolymer | 7.5 | 7.5 | 7.5 | | | 2 | 2 |
| Dimethicone (And) Dimethicone/Vinyl Dimethicone Crosspolymer | 3.5 | 3.5 | 3.5 | 3.5 | 3.5 | 3.5 | 3.5 |
| Water | 10 | 10 | | | | | |
| Glycerin | 15 | 15 | 15 | 15 | 15 | 15 | 15 |
| Caprylyl Glycol | 0.3 | 0.3 | 0.3 | 0.3 | 0.3 | 0.3 | 0.3 |
| Butyl Methoxydibenzoylmethane | | | | | | | |
| Ethylhexyl Salicylate | | | | | | | |
| ZINC OXIDE (And) TRIETHOXYCAPRYLYLSILANE | 7 | 5 | 4.103 | 4.103 | 4.103 | 4.103 | 4.103 |
| Octocrylene | | | | | | | |
| Homosalate | | | | | | | |
| Titanium Dioxide | | | 12.58 | 12.58 | 12.58 | 12.58 | 12.58 |
| Titanium Dioxide (And) Silica | 9 | 9 | | | | | |
| Polyglyceryl-4 Diisostearate/ Polyhydroxystearate/Sebacate | | | | | | | |
| Panthenol | 5 | 5 | 5 | 5 | 5 | 5 | 5 |
| Water | 5.15 | 10.15 | 12.967 | 18.467 | 17.717 | 16.467 | 15.717 |

Example 2

SPF Testing of Inventive composition 1 and the comparative control which lacks film former.

TABLE 3

SPF Values

| | Inventive Example (INV 1) | Comparative Example (INV 1 without film formers) |
|---|---|---|
| SPF | 25.37 | 11.46 |
| SPF | 26.75 | 11.97 |
| AVG SPF | 26.06 | 11.71 |

As shown in Table 3, the inventive composition (INV 1) which includes the combination of film formers and silicone blend showed an SPF of 26.06 while the comparative composition lacking the film formers showed an SPF of 11.71, demonstrating that incorporation of film former with the UV system and the silicone blend enhances in vitro SPF reading by over 100%.

The Water Break Test

The water break property is unique to a water-in-silicone emulsion. When the formula is spread on the skin, the water is forced out of the emulsion, thus resulting in a water break feel. This water break can also be visualized as water droplets form on the skin after rubbing. The water break test is performed to evaluate the perceivable level of water breaking from the formula. By rubbing the formula on the skin, both a visual and sensorial level of water break are determined.

About 0.2 g of a water-in-oil emulsion sample of cosmetic composition is taken and placed on the back of a hand, then it is applied thereon by circling gently with the middle finger and ring finger of the other hand, and then the phenomenon of the water-releasing effect is observed when the circling application reaches 20 cycles. With respect to the present invention, a good water-releasing effect of the emulsion means that the water-releasing effect has an evaluation result wherein from about 2 to about 10 bead-like water drops having an average diameter of more than or equal to 3 mm appear, or from about 2 to about 20 bead-like water drops having an average diameter of more than or equal to 1 mm appear.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A sunscreen composition, comprising:
    a) a silicone phase that comprises:
        1) two or more silicone film formers present from about 0.1% to about 5.0% by weight, based on the total weight of the composition; and
        2) a blend of silicones present from about 20% to about 35% by weight, based on the total weight of the composition, the blend of silicones comprising at least one of each of:
            i. a low viscosity silicone fluid;
            ii. at least one silicone co-emulsifier; and
            iii. at least one self-emulsifying silicone elastomer; and
    b) a UV filter system that comprises one or more UV filters, the UV filter system present from about 20% to about 30% by weight, based on the total weight of the composition,
    wherein the two or more silicone film formers and blend of silicones are present in quantities sufficient such that the composition has an SPF that is boosted by at least 100% as compared to a composition that lacks silicone film former.

2. The sunscreen composition according to claim 1, wherein:
    a) the at least one silicone fluid is present from about 5% to about 20% by weight;
    b) the at least one silicone co-emulsifier is present from about 0.1% to about 2.0% by weight; and
    c) the at least one self-emulsifying silicone elastomer is present from about 2% to about 15% by weight,
    each based on the total weight of the composition.

3. The sunscreen composition according to claim 1, wherein the UV filter system comprises at least one or a combination of inorganic UV filters, or at least one or a combination of organic UV filters.

4. The sunscreen composition according to claim 1, wherein the UV filter system comprises one or more UV filters selected from the group consisting of inorganic UV filters and organic UV filters, wherein:
    a) inorganic UV filters are selected from the group consisting of:
        1) titanium dioxide;
        2) Zinc oxide;
        3) titanium dioxide (and) silica; and
        4) a combination thereof; and
    b) organic UV filter are selected from the group consisting of:
        1) butyl methoxydibenzoylmethane;
        2) ethylhexyl salicylate;
        3) triethoxycaprylylsilane;
        4) octocrylene;
        5) homosalate; and
        6) a combination thereof.

5. The sunscreen composition according to claim 1, wherein the two ore more silicone film formers comprise a silicone acrylate co-polymer.

6. The sunscreen composition according to claim 1, wherein the two or more silicone film formers comprise:
   a) dimethicone (and) dimethiconol present from about 0.5% to about 2.0% by weight based on the total weight of the composition; and
   b) dimethicone (and) acrylates/dimethicone copolymer present from about 2.0% to about 2.5% by weight based on the total weight of the composition.

7. The sunscreen composition according to claim 1, wherein the at least one low viscosity silicone fluid in the blend of silicones comprises one or more volatile and nonvolatile silicone oils.

8. The sunscreen composition according to claim 1, wherein the at least one silicone fluid in the blend of silicones comprises dimethicone present from about 5% to about 18% by weight based on the total weight of the composition.

9. The sunscreen composition according to claim 1, wherein the at least one silicone co-emulsifier is selected from polyether-modified silicones.

10. The sunscreen composition according to claim 1, wherein the at least one silicone co-emulsifier in the blend of silicones comprises lauryl PEG-9 polydimethylsiloxyethyl dimethicone present from about 0.2% to about 0.7% by weight based on the total weight of the composition.

11. The sunscreen composition according to claim 1, wherein the at least one self-emulsifying silicone elastomer in the blend of silicones comprises a substituted or unsubstituted dimethicone crosspolymer.

12. The sunscreen composition according to claim 1, wherein the at least one self-emulsifying silicone elastomer in the blend of silicones comprises:
   a) dimethicone (and) dimethicone/vinyl dimethicone crosspolymer present from about 2% to about 15% by weight based on the total weight of the composition;
   b) dimethicone (and) dimethicone/polyglycerin-3 crosspolymer present from about 4% to about 10% by weight based on the total weight of the composition;
   c) dimethicone (and) dimethicone/PEG-10/15 crosspolymer present from about 3% to about 7% by weight based on the total weight of the composition;
   d) dimethicone (and) dimethicone crosspolymer present from about 4% to about 8% by weight based on the total weight of the composition; or
   e) a combination thereof.

13. The sunscreen composition according to claim 1, wherein the composition is a water-in-silicone emulsion that comprises an aqueous phase.

14. The sunscreen composition according to claim 13, the aqueous phase comprising: a hydrating agent present from about 5% to about 25% by weight, based on the total weight of the composition; and water from about 25% to about 60% by weight based on the total weight of the composition.

15. The sunscreen composition according to claim 14, wherein the hydrating agent is glycerin present from about 10% to about 18% by weight based on the total weight of the composition.

16. The sunscreen composition according to claim 15, further comprising one or more of a surfactant, a cosmetic powder, or an emollient, and wherein the UV system comprises one or a combination of organic UV filters selected from the group consisting of:
   1) butyl methoxydibenzoylmethane;
   2) ethylhexyl salicylate;
   3) zinc oxide (and) triethoxycaprylylsilane;
   4) octocrylene;
   5) homosalate; and
   6) a combination thereof.

17. A sunscreen composition, comprising:
   a) a silicone phase that comprises:
      1) at least one silicone acrylate film former present from about 0.1% to about 5.0% by weight, based on the total weight of the composition; and
      2) a blend of silicones present from about 20% to about 35% by weight, based on the total weight of the composition, the blend of silicones comprising at least one of each of:
         i. a low viscosity silicone fluid present from about 5% to about 20% by weight;
         ii. a silicone co-emulsifier present from about 0.1% to about 2.0% by weight; and
         iii. a self-emulsifying silicone elastomer present from about 2% to about 15% by weight,
         each based on the total weight of the composition;
   b) a UV filter system that comprises one or more UV filters, the UV filter system present from about 20% to about 30% by weight, based on the total weight of the composition; and
   c) an aqueous phase comprising: a hydrating agent present from about 5% to about 25% by weight, based on the total weight of the composition; and water from about 25% to about 60% by weight based on the total weight of the composition,
   wherein the silicone film former and blend of silicones are present in quantities sufficient to provide an SPF that is boosted by at least 100% as compared to a composition that lacks silicone film former.

18. The sunscreen composition according to claim 17, the composition further comprising one or more of a surfactant, a cosmetic powder, or an emollient, and wherein the UV system comprises one or a combination of organic UV filter selected from the group consisting of:
   1) butyl methoxydibenzoylmethane;
   2) ethylhexyl salicylate;
   3) zinc oxide (and) triethoxycaprylylsilane;
   4) octocrylene;
   5) homosalate; and
   6) a combination thereof.

19. The sunscreen composition according to claim 17, wherein the UV filter system comprises one or a combination of inorganic UV filters selected from the group consisting of:
   1) titanium dioxide;
   2) titanium dioxide (and) silica; and
   3) a combination thereof,
   wherein the hydrating agent is glycerin and is present from about 10% to about 18% by weight based on the total weight of the composition.

20. A sunscreen composition, comprising:
   a) a silicone phase that comprises:
      1) at least one silicone film former present from about 0.1% to about 5.0% by weight, based on the total weight of the composition; and
      2) a blend of silicones present from about 20% to about 35% by weight, based on the total weight of the composition, the blend of silicones comprising at least one of each of:
         i. a low viscosity silicone fluid;
         ii. at least one silicone co-emulsifier including lauryl PEG-9 polydimethylsiloxyethyl dimethicone present from about 0.2% to about 0.7% by weight based on the total weight of the composition; and
iii. at least one self-emulsifying silicone elastomer; and
b) a UV filter system that comprises one or more UV filters, the UV filter system present from about 20% to about 30% by weight, based on the total weight of the composition, wherein the silicone film former and blend of silicones are present in quantities sufficient such that the composition has an SPF that is boosted by at least 100% as compared to a composition that lacks silicone film former.

* * * * *